United States Patent [19]

Kirsch et al.

[11] Patent Number: 5,418,144
[45] Date of Patent: May 23, 1995

[54] SPINDLE POLE BODY SCREEN FOR FUNGICIDES

[75] Inventors: Donald R. Kirsch, Princeton; Margaret H. K. Lai, East Brunswick, both of N.J.

[73] Assignee: American Cyanamid Company, Wayne, N.J.

[21] Appl. No.: 66,764

[22] Filed: May 25, 1993

[51] Int. Cl.$^6$ .................. C12Q 1/18; C12N 1/00
[52] U.S. Cl. ........................ 435/32; 435/29; 435/34; 435/69.9; 435/172.1; 435/255.1; 435/942
[58] Field of Search ............ 435/32, 29, 34, 69.9, 435/172.1, 255.1, 256.1, 942, 255.2, 33

[56] References Cited

PUBLICATIONS

Baum, P., et al., Yeast Cell Biology, Alan R. Liss, Inc., New York, 1986, pp. 151–158.
Baum, P., et al., Mol. Cell. Biol. 8: 5386–5397 (1988).
Hartwell, L. H., J. Bact., 93: 1662–1670 (1967).
Koeller, W., and Scheinpflug, H., Plant Disease, 71: 1066–1074 (1987).
Masui, Y., et al., Biochem. Biophys. Res. Com. 78: 534–538 (1977).
May, G. S., et al., J. Biol. Chem. 267: 15737–15743 (1992).
Mortimer, R. K., and Schild, D., Microbiol. Rev. 49: 181–212 (1985).
Rose, M. D., and Fink, G. R., Cell 48: 1047–1060 (1987).
Sherman, F., et al., Methods in Yeast Genetics, Cold Spring Harbor, New York, 1974, pp. 4 to 8.
Snyder, M., and Davis, R. W., Cell 54: 743–754 (1988).
McGrew et al, Biological Abstracts, vol. 95, No. 7, Ref. No. 73955 (1992) (Mol. Biol. Cell 3(12) 1443–1454, 1992).
Mortimer et al, Microbiol. Rev., vol. 49, pp. 181–212, 1985.
Kim et al, Genetics, vol. 126, pp. 799–812, Dec. 1990.

Primary Examiner—David A. Redding
Assistant Examiner—Abdel A. Mohamed
Attorney, Agent, or Firm—Darryl L. Webster; Alan M. Gordon; Mary M. Krinsky

[57] ABSTRACT

A method for the identification of agents which inhibit spindle pole body formation or function, thus exhibiting selective fungicidal activity, involves the incubation of test samples in cultures of a *Saccharomyces cerevisiae* strain that produces excess numbers of spindle pole bodies. Cultures containing samples that inhibit spindle pole bodies exhibit enhanced growth because the growing yeast is rescued from the adverse effects of excess spindle bodies. In the preferred practice of the invention, the test sample is added to a *S. cerevisiae* culture or culture area containing a strain that has a conditional mutation producing excess spindle pole bodies, such as diploid esp1-1 strains. The culture or culture area is preincubated under permissive conditions wherein the strain can grow to some extent, and then conditions are shifted to restrictive conditions so that the mutant strain either cannot grow or grows poorly. The extent of growth in the culture or culture area containing test sample is then compared with the extent of growth in the absence of test sample, and the presence of spindle pole body inhibition is determined by observation of whether culture growth in the presence of test sample exceeds growth in its absence. Preferred embodiments employ test samples on disks or in wells in solidified cultures, facilitating easy visual inspection of growth. A presumptive spindle pole body inhibitor, identified in random screening, is used as a positive control which can be compared to the test sample.

23 Claims, No Drawings

SPINDLE POLE BODY SCREEN FOR FUNGICIDES

TECHNICAL FIELD OF THE INVENTION

This invention relates to a screening method for the identification of agents that inhibit spindle pole body formation and/or function and more particularly relates to a screening method for the identification of potential fungicides that inhibit spindle pole body formation and/or function.

BACKGROUND OF THE INVENTION

The search for agents which can effectively act against fungi and mycoses injurious to plants and animals in a suitably selective manner such that the host plant or animal is not significantly harmed can be an expensive and time-consuming process. A significant degree of trial and error normally is required in order to ascertain even potential candidates among a wide variety of possibilities, and thereafter to further determine whether those with potential in fact exhibit the requisite activity and selectivity suitable for commercial use. Much advantage could be realized were it possible to provide a relatively rapid and precise method for screening a wide variety of possible agents based upon some specific characteristic or property useful as a predictor of anti-fungal activity and fungal specificity. Apart from the evident economic advantages, a method of this type would enable larger universes of possible agents to be screened, with corresponding increased potential for identifying particularly suitable fungicides. This is particularly important as increasing numbers of injurious fungi are becoming resistant to commercially available fungicides (Koeller, W., and Scheinpflug, H., *Plant Disease*, 71: 1066–1074 (1987)).

As discussed in detail hereinafter, the present invention provides a screening process which is based upon the finding that chemical and biological agents having fungicidal activity can be identified based upon their ability to inhibit spindle pole body formation and/or function in yeast strains that otherwise overproduce spindle pole bodies.

The accurate segregation of chromosomes during mitosis is essential for normal eukaryotic cell division, and precisely organized complex microtubule arrays are required during this process so that reproduction is faithful. Chromosome segregation is mediated by the mitotic spindle apparatus which comprises the spindle microtubules, the kinetochore (a structure attaching spindle fibers to chromosomes), and the spindle pole, which organizes the microtubules. In mammals and some other organisms, the spindle pole equivalent is the centrosome; it comprises the centrosphere and a pair of centrioles. In yeast and other fungi, the spindle pole is called the spindle pole body; it is permanently associated with the nuclear envelope because the nuclear envelope does not disassemble during yeast mitosis.

Spindle pole bodies in yeast not only function in the formation of the mitotic spindle, but also serve crucial roles in karyogamy (fusion of gametic nuclei), where they mediate the initiation of nuclear fusion within the zygotes and in the formation of spore walls (Baum, P., et al., *Yeast Cell Biology*, Alan R. Liss, Inc., New York, 1986, pages 151–158). Microtubules originating from the yeast spindle pole body have been implicated in other cellular processes, including bud formation and/or growth (Snyder, M., and Davis, R. W., *Cell* 54: 743–754 (1988)). Therefore, it is essential that the behavior of yeast spindle pole bodies be highly integrated with other cellular functions.

Whereas the mammalian centriole is defined microscopically as a roughly spherical symmetrical cytoplasmic structure, the fungal spindle pole body is a planar structure embedded in the nuclear membrane. Plant cells have no functional equivalent of a spindle pole body visible by microscopy. Besides these differences in morphology and cellular location, the existence of agents with differential action on fungal and mammalian microtubules such as griseofulvin and benomyl argues for differences in the mitotic apparatus in these cell types.

Cellular division in yeast, especially common baker's yeast *Saccharomyces cerevisiae*, has been studied for decades, and the genetics of this organism is very well developed (see Mortimer, R. K., and Schild, D., *Microbiol. Rev* 49: 181–212 (1985), for example, for a genetic map). Having a low DNA content, short generation times, ease of cultivation and preservation, simplicity of nutritional requirements and rapid growth, yeast is readily amenable to genetic analysis and manipulation using classical and molecular techniques.

At least four genetic loci have been described which affect spindle pole body synthesis in yeast. One is a cell division cycle (cdc) mutant, cdc31, which uncouples spindle pole body duplication from other aspects of cell division (Baum, et al., cited above). Spindle pole body duplication fails to occur despite the occurrence of budding and DNA replication.

Rose, et al., have characterized a gene implicated in mutations that prevent karyogamy, denoted KAR1, and shown that it is required for both mitosis and conjugation (Rose, M. D., and Fink, G. R., *Cell* 48: 1047–1060 (1987)). The KAR1 product is apparently required for mitosis, spindle body duplication, and the assembly of both intranuclear and extranuclear microtubules. Overproduction of the gene product blocks spindle pole body duplication. Mutant strains show defects both in spindle body duplication and chromosome disjunction. Both mitotic and mating mutant cells have defects associated with the spindle plaque. Cells arrested in mitosis by either insufficient or excess KAR1 gene product are unable to duplicate spindle plaque, and loss of KAR1 function results in abnormally long extranuclear microtubules. Microtubules of abnormal length are also found in kar1-1 cells during the mating process.

Baum, et al., identified a gene denoted ESP1 for extra spindle pole bodies which functions in the duplication of the spindle pole body (Baum, et al., cited above, and Baum, P., et al., *Mol. Cell. Biol.* 8: 5386–5397 (1988)). The investigators created a number of mutant strains, including one having a temperature-sensitive lethal mutation that deregulated spindle pole duplication. At permissive temperatures (~23° C.), the mutant grew normally. At restrictive temperatures (above 34.5° C.; 36° C. was used in most experiments reported), growth, as evidenced by DNA synthesis and cell division, was arrested, and the cells continued to increase their number of spindle pole bodies incessantly. Large numbers of spindle pole bodies accumulated in the yeast, an effect that was lethal to most of the cells.

Snyder and Davis (cited above) identified and cloned a spindle pole body gene using an immunoscreening technique and denoted it SPA1 for spindle pole antigen. The gene product, which is overproduced in esp1-1 mutants and cofractionates with the yeast nuclear envelope, apparently is a protein associated with the yeast spindle pole. Mutant strains exhibit a high frequency of chromosome nondisjunction, abnormal spindles, and chromosome mis-segregation. A mutational analysis indicates the gene product to be important for cell growth, chromosome segregation, and other cellular processes.

Summary of the Invention

It is an object of the invention to provide a screening test for identifying agents that inhibit spindle pole body formation and/or function.

It is a further and more specific object of the invention to provide a screening test for identifying potential fungicidal agents based upon the ability of the agent to inhibit spindle pole body formation and/or function.

These and other objects are accomplished by the present invention, which provides a screening method for identifying potential fungicides, based upon determination that they inhibit spindle pole body formation and/or function. In the method, agents are incubated in a culture of a yeast mutant having a defect in spindle pole body formation wherein spindle poles are overproduced, which is normally detrimental or fatal to the cells. Agents that inhibit spindle pole body formation in these mutants are identified as possessing selective fungicidal activity. In preferred embodiments, agents possessing fungicidal activity rescue the cells from otherwise lethal spindle pole body overproduction, and cultures containing these agents exhibit enhanced yeast cell growth relative to a control.

In the practice of the invention, a test sample (i.e., an agent being tested to determine whether it exhibits an inhibition of spindle pole body formation and/or function) is added to a culture or culture area of a conditional mutant strain of *Saccharomyces cerevisiae* which produces excess numbers of spindle pole bodies. The culture is preincubated with the test sample under permissive conditions for such time under such conditions sufficient to observe some yeast cell growth. The culture is then shifted to restrictive conditions and incubated for such time under such conditions as would be sufficient to observe a diminution or cessation of growth in a corresponding culture or culture area containing no test sample. The extent of growth in the culture or culture area containing test sample is then compared with the extent of growth in a culture or culture area containing no test sample. The presence of spindle pole body inhibition is determined by observation that culture growth in the presence of test sample exceeds growth in its absence.

Yeast strains that can be employed in the practice of this invention include esp1 mutants and other mutants that overproduce spindle pole bodies. In a preferred screening test, the yeast strain employed is a diploid *Saccharomyces cerevisiae* strain homozygous for a conditional lethal temperature-sensitive esp1-1 mutation. Active agents are identified by the observation of enhanced growth of the cultured yeast after preincubation at the permissive temperature followed by incubation at the restrictive temperature. In one embodiment, a spindle pole body inhibitor is employed as a positive control to assist in the identification of active agents.

In a particularly preferred embodiment, the yeast mutant is grown in a solidified media in a plate or dish, so that test samples can be observed visually and simultaneously as regions of the same culture. Actives produce a turbid zone of growth around the test sample.

DETAILED DESCRIPTION OF THE INVENTION

This invention is based upon the finding that chemical and biochemical agents of potential value as fungicides can be identified in a *Saccharomyces cerevisiae* mutant exhibiting an overproduction of spindle pole body formation. Cultures containing test samples that inhibit spindle pole body formation or function exhibit enhanced growth because the test sample rescues the cultured yeast cells from the deleterious effects of the mutant.

In the practice of this invention, a chemical or biochemical test sample is added to a culture or culture area of a strain of baker's yeast, *Saccharomyces cerevisiae*, that produces excess numbers of spindle pole bodies. Several such strains have been described, including esp1 mutants and cdc-esp1 double mutants (see the Baum papers, cited above). Any strain that overproduces spindle pole bodies can be employed, including the ones mentioned above and other esp1 double mutants, but conditional mutant strains, notably temperature-sensitive mutants, are preferred. A "conditional mutant" is a mutant that exhibits the appearance and growth characteristics of wild-type phenotype under certain, permissive environmental conditions, but exhibits a mutant phenotype under other, restrictive conditions.

"Temperature-sensitive" mutants are those that exhibit mutation only in a limited temperature range. Typically, gene control is affected above a certain temperature or the product of such a gene functions normally, but is unstable above a certain temperature. An advantage of temperature-sensitive mutants is that they are easy to use; the mutants are readily grown in culture at a permissive temperature and then the same culture are shifted to a restrictive temperature for expression of the mutation.

In the generalized method of this invention, a test sample is added to a culture of a mutant strain of *S. cerevisiae* that overproduces spindle pole bodies and the culture is incubated for such time under such conditions to observe yeast cell growth. Positive samples in the screen inhibit spindle pole body duplication; this is typically reflected as enhanced culture growth. The effect a test sample has on spindle pole body formation, however, is observed using any means, including direct or indirect comparisons of spindle pole body abundance. Direct methods include, but are not limited to, localization of spindle pole bodies by light microscopy, and indirect methods include, but are not limited to, immunofluorescence using antitubulin antibody.

In a preferred method of this invention, the growth characteristics of a conditional lethal mutant overproducing spindle pole bodies are assayed in: (1) the presence of a test sample, and (2) in the absence of a test sample, and the results are compared. A test sample is added to a culture of a conditional mutant *S. cerevisiae* strain that overproduces spindle pole bodies. The culture is preincubated under permissive conditions to obtain some yeast growth, and then shifted to restrictive conditions and incubated to observe spindle pole body overproduction. The extent of growth in the culture (or culture area) containing the test sample is then compared with the extent of growth in a corresponding culture (or culture area) containing no test sample.

Spindle pole body inhibition is determined by observation of enhanced growth in the presence of test sample.

A *S. cerevisiae* strain particularly adapted to the practice of this invention is a temperature-sensitive strain denoted SN127d constructed and described by Baum, 1988, cited above. Diploid SN127d is the product of a cross between meiotic segregants derived from a cross between strain 21-1 and another strain as described in Baum, 1988, which are constructed, sporulated and analyzed using standard procedures described by by Sherman, F., et al. (*Methods in Yeast Genetics*, Cold Spring Harbor, N.Y., 1974).

Briefly stated, SN127d is obtained in a screen for mutations that cause diploidization of haploid cells. Cultures of a wild-type strain growing exponentially in standard media are subjected to mutagenesis by suspending in buffer, treating with ethylmethanesulfonate, and agitating under conditions yielding 80% viability. After quenching, the cells are diluted into fresh media and grown overnight at 23° C. to overcome possible phenotypic lag in expression of the mutant phenotype. The exponentially growing cultures are then subjected to 36° C. for 6 hours (about 2 generations of growth) to induce diploid formation by potential mutants. The cells are again incubated at 23° C. for 12 to 18 hours and transferred to sporulation medium at a density of $1 \times 10^6$ to $2 \times 10^6$ cells per ml. After a 3-day incubation at 23° C. with aeration, the cultures are subjected to diethyl ether selection for ascospores by sedimenting the cells, suspending them in 1/10 volume of 0.2M potassium acetate (pH 5.0), and mixing them with an equal volume of diethyl ether for 10 minutes The aqueous phase containing the cells is withdrawn, and the cells are washed twice with distilled water by centrifugation and resuspension before being plated and grown for 4 days at 23° C.

Colonies are shifted from exponential growth at 23° C. to 36° C., and plates screened for growth at 36° C. by replica plating. Temperature-sensitive colonies are picked into liquid media and again subjected to the restrictive temperature pulse and sporulation regimen. One of the 22 colonies treated this way, denoted strain 21-1, gives rise to microscopically detectable spores. The strain is temperature sensitive for growth, and failed to form colonies at temperatures above 34.5° C. The genetic lesion for multiple spindle bodies in this strain, denoted esp1-1, is characterized using sporulation and found to co-segregate with temperature sensitivity in every case. The homozygous mutant diploid strain derived from 21-1 is denoted SN127d, and the heterozygote, SN127h.

Thus, SN127d is a diploid *Saccharomyces cerevisiae* strain homozygous for the esp1-1 mutation. At permissive temperatures, e.g., ~23° C., the yeast mutant grows normally. Cells shifted to restrictive temperatures, e.g., ~36° C., repeatedly duplicate their spindle pole bodies, and become unable to continue DNA synthesis and cell division. The lethal effect of the mutation is irreversible after about two hours at the restrictive temperature.

In an especially preferred practice of this invention, a chemical or biochemical test sample is added to a culture of SN127d. The test sample is introduced to a disk or a well on a culture plate in a standard diffusion assay using solidified media, or introduced into one of a series of equivalent tissue culture tubes or bottles in a standard turbidity assay using liquid media. Solidified cultures are preferred so that growth can be easily observed by visual inspection. The culture is preincubated for such time under such conditions sufficient to observe some yeast cell growth at the permissive temperature (~20° C. to ~25° C.). The preincubation period is typically one to three (e.g., 2) hours. The culture is then shifted to the restrictive temperature (~35° to ~37° C.) and incubated for such time under such conditions sufficient to observe spindle pole overproduction, and thus yeast cell growth inhibition, in corresponding cultures or culture areas having no test sample. The incubation period is typically a few hours to a few days (e.g., 2 days). The extent of growth in the culture containing or surrounding the test sample is compared with the extent of growth in a culture or culture area containing no test sample. The presence of inhibition of spindle pole body duplication or function is determined by observing whether growth in the presence of test sample exceeds growth in its absence. In a culture plate, this is a turbid zone of growth surrounding the test sample in the culture lawn. In a culture tube series, this is enhanced turbidity, which is generally determined by measuring optical density (OD) at 550 to 50 nm.

In one embodiment, the method employs a spindle pole body inhibitor as a positive control. The control is useful in discerning whether the screen is functioning properly and in identifying positives by direct comparison. No synthetic or natural compound has heretofore been reported to inhibit spindle pole body duplication or function, but a positive compound is found in a screening of over 17,000 compounds using the spindle pole body screen (see the Examples below). In a disk or well diffusion assay, this is introduced to a disk or a well in the culture plate at the same time the test sample is introduced. After the preincubation and incubation periods, growth in the vicinity of the control or in the control culture exceeds growth in a culture where there is no test sample.

Any type of solidified or liquid media that will support growth and reproduction of the *S. cerevisiae* strain may be employed in cultures for practicing the method of this invention. Numerous yeast media are known to the skilled artisan, and an advantage of the invention is that baker's yeast is relatively easy to grow. Typical media are yeast extract, peptone and dextrose (YEPD) or yeast extract and dextrose (YED) media; yeast basal growth media (YBGM) containing glucose, vitamins, minerals, and water; yeast, peptone, and adenine sulfate (YPA) media; yeast mannitol (YM) media and YM plus glucose and variations thereof, including YM-1 containing yeast extract, peptone, a yeast nitrogen base, uracil, succinic acid, and glucose (described by Hartwell, L. H., *J. Bact.*, 93: 1662–1670 (1967), used by Baum, et al, 1988, cited above, for SN127d); synthetic dextrose (SD) media containing dextrose, a yeast nitrogen base, and water and optionally containing amino acids, adenine sulfate and uracil; and the like. Preferred media are solidified by adding agar or gelatin; especially preferred are agar solidified media.

Though mating factors of *S. cerevisiae* generally arrest the cell division cycle, they permit continuous growth, and extra spindle pole bodies or multipolar spindles are formed when some cdc-esp1 double mutants are grown in factor-enriched media (described by Baum, et al., 1986, cited above). Hence, mating factors may may be added to enrich the cultures in some embodiments. Typical mating pheromones include the native α-mating factor, which can be isolated, prepared, or obtained commercially, and active truncated versions of the peptide (Masui, Y., et al., *Biochem. Biophys. Res. Com.* 78: 534–538 (1977)).

The screening method of the invention has numerous advantages, including speed and simplicity. A large number of samples are tested quickly and inexpensively. The screening method is also selective for compounds acting on spindle pole bodies, and can thus target agents which act against potentially harmful fungi without harming host plants or animals. The spindle pole body screen is sensitive, and small amounts of biochemical or chemical agents are tested. In a standard assay, for example, which employs solidified media in a plate as described in the examples below, as little as 20 μg of a biochemical or chemical test sample or control can be applied to a disk or in a well. For fermentation broths, however, concentration may be necessary.

The screening method of this invention is a low positive rate assay (<0.02%), so that secondary tests are not of crucial importance. However, where these are employed to prioritize actives, standard in vitro and in vivo fungicide discovery screens are useful. In vitro screens test samples for their ability to inhibit the growth of selected phytopathogenic fungi cultured in nutrient agar. These include fungi causing wheat eyespot (*Pseudocercosporella herpotrichoides*), rice sheath blight (*Rhizoctonia solani*) and damping off (*Fusarium oxysporum*); all synthesize spindle pole bodies. High potency fungicides are active against these species in the 10 ppm range (10 μg/ml).

In in vivo screens, a variety of phytopathogenic fungi are used to infect plants treated with test compounds. Active compounds block or reduce the appearance of disease symptoms. A number of model plant infections can be employed in the screen and include fungi having spindle pole bodies that cause apple scab (*Venturia inaequalis*), pepper botrytis (*Botrytis cincerea*), rice blast (*Pyricularia oryzae*), sugar beet cercospora (*Cercospora beticola*), tomato early blight (*Alternaria solani*), wheat leaf rust (*Puccinia recondita tritici*), and wheat powdery mildew (*Erysiphe graminis tritici*).

EXAMPLES

The following examples are presented to further illustrate and explain the present invention and should not be taken as limiting in any regard. The examples describe a model fungicide assay employing the method of this invention using the SN127d mutant yeast strain.

YEPD media is prepared by mixing the following cell culture tested components obtained from Difco:

| | |
|---|---|
| Yeast Extract | 10 gm |
| Peptone | 20 gm |
| Dextrose | 20 gm |
| Agar | 20 gm |
| Distilled Water | 1000 ml | and autoclaving at 20 lbs for 15 minutes.

One part of a culture of SN127d, grown in YEPD media to a final $OD_{600}$ of 5 or greater, is added to 100 parts media. Plates are poured and samples applied on disks (20 μg/disk). The plates are incubated at room temperature for two hours and then shifted to 35° C. and incubated for two days. Actives promote a zone of growth above the background turbidity.

A large number of compounds are tested using this assay, including a panel of fungicides selected to represent diverse mechanisms of action. A screen of 30 fungicides and herbicides with varied mechanisms of action (Table I) and a panel of 70 random antibiotics (Table II) are tested.

TABLE I

| STANDARD FUNGICIDE PANEL | |
|---|---|
| Compound | Target |
| bcamphotericin B | plasma membrane (polyene) |
| cerulenin | fatty acid biosynthesis |
| haloprogin | respiration |
| ketoconazole | ergosterol biosynthesis (lanosterol 14α-demethylase) |
| miconazole | ergosterol biosynthesis (lanosterol 14α-demethylase) |
| dinaconazole | ergosterol biosynthesis (lanosterol 14α-demethylase) |
| econazole | ergosterol biosynthesis (lanosterol 14α-demethylase) |
| fenarimole | ergosterol biosynthesis (sterol Δ14 reductase) |
| tridemorph | ergosterol biosynthesis (sterol Δ14 reductase) |
| tolnaftate | ergosterol biosynthesis (squalene monooxygenase) |
| U18666A | ergosterol biosynthesis (squalene cyclase) |
| cycloheximide | protein biosynthesis |
| polyoxin D | chitin biosynthesis (cell wall) |
| nikkomycin | chitin biosynthesis (cell wall) |
| nocodazole | microtubule |
| benomyl | microtubule |
| maneb | multi-target |
| metalaxyl | rRNA biosynthesis |
| vinclozolin | lipid peroxidation |
| kanamycin | mitochondria |
| tunicamycin | glycoprotein biosynthesis |
| carboxin | succinate dehydrogenase |
| cyanobutarate | microtubule (plant) |
| antimycin | respiration |
| 5-fluoro-cytosine | nucleotide metabolism |
| glyphosate | herbicide (aromatic amino acid biosynthesis) |
| phosphinothricin | herbicide (glutamine biosynthesis) |
| aminotriazole | herbicide (histidine biosynthesis) |
| sulfometuron methyl | herbicide (branched chain amio acid biosynthesis) |
| pendimethalin | herbicide (microtubule) |

TABLE II

| STANDARD ANTIBIOTIC PANEL | |
|---|---|
| pimaricin (tennecetin) | streptogramin ("type") |
| monazomycin | nystatin |
| aspartocin | bacitracin |
| clavacin | citrinin |
| avoparcin | isoquinocycline |
| neutramycin | A1531 |
| leucomycin | AO341β |
| angustmycin A & C | gliotoxin |
| gibberellic acid | puromycin |
| puromycin aminonucleoside | BM123α |
| etamycin | mocimycin |
| neomycin | viomycin |
| netropsin | lincomycin |
| picromycin | A9537 |
| AN272α | levomycin |
| AM374 | antiprozoin |
| BL580 zeta | actithiazic acid |
| hamycin | carbomycin |
| frenolicin | fusarinic acid |
| BL580α | tylosin |
| declomycin | teterahydro spiramycin |
| usnic acid | geldanamycin |
| Z1220A | BM782ε |
| BO2964 complex | choramphenicol |
| A8363 | actinomycin |
| BM123γ | AD97 |
| phenazine α | paromomycin |
| streptomycin | A4825 |
| alazopeptin | nucleocidin |
| nonactin | valinomycin |
| C19004 complex | avilamycin |

TABLE II-continued

STANDARD ANTIBIOTIC PANEL

| V214W | V214X |
|---|---|
| vancomycin | ristocetin |
| relomycin | CO8078α |
| blasticidin S | 4-dedimethylamino-4-methylamino-anhydrotetracycline |

No actives are found in testing the compounds of Table I and II. A panel of 16,679 additional compounds produces one active.

In secondary tests, the compound exhibits antifungal activity and rescues *Aspergillis nidulans* bimB3 mutants, which apparently have structurally defective spindle pole bodies and thus are the *A. nidulans* equivalent of esp1 mutants (May, G.S., et al., *J. Biol. Chem.* 267: 15737–15743 (1992)), thus confirming the utility of the compound as a positive control. In assays of this invention, the compound is employed as a control at levels of about 20 μg/disk.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are meant to cover the claimed components and steps in any sequence which is effective to meet the objectives there intended, unless the context specifically indicates the contrary.

BIBLIOGRAPHY

Baum, P., et al., *Yeast Cell Biology*, Alan R. Liss, Inc., New York, 1986, pages 151–158.
Baum, P., et al., *Mol. Cell. Biol.* 8: 5386–5397 (1988).
Hartwell, L. H., *J. Bact.*, 93: 1662–1670 (1967).
Koeller, W., and Scheinpflug, H., *Plant Disease*, 71: 1066–1074 (1987).
Masui, Y., et al., *Biochem. Biophys. Res. Com.* 78: 534–538 (1977).
May, G. S., et al., *J. Biol. Chem.* 267: 15737–15743 (1992).
Mortimer, R. K., and Schild, D., *Microbiol. Rev.* 49: 181–212 (1985).
Rose, M. D., and Fink, G. R., *Cell* 48: 1047–1060 (1987).
Sherman, F., et al., *Methods in Yeast Genetics*, Cold Spring Harbor, N.Y., 1974, pages 4 to 8. Snyder, M., and Davis, R. W., *Cell* 54: 743–754 (1988).

We claim:

1. A screening method for identifying fungicides, said method comprising:
    (a) adding a sample agent to a culture of a *Saccharomyces cerevisiae* strain that normally produces excess numbers of spindle pole bodies, thereby providing a sample culture;
    (b) incubating said sample culture for a period of time and under conditions sufficient to observe yeast cell growth; and
    (c) comparing growth in said sample culture with a corresponding first control culture of said strain containing no sample agent and identifying said sample agent as a fungicide by observation that the sample culture produces greater growth than that observed in the first control culture.

2. A method according to claim 1 wherein said *S. cerevisiae siae* strain is an esp1 mutant.

3. A method according to claim 2 wherein said *S. cerevisiae siae* strain is a cdc-esp1 double mutant.

4. A method according to claim 3 wherein a *S. cerevisiae* mating factor is added to the cultures prior to incubation.

5. A method according to claim 2 wherein said strain is a diploid *S. cerevisiae* strain homozygous for a conditional lethal temperature-sensitive esp1-1 mutation.

6. A method according to claim 5 wherein said strain is SN127d.

7. A method according to claim 5 wherein said sample culture is preincubated for a period of time at a permissive temperature sufficient to observe yeast cell growth and then is incubated at a restrictive temperature.

8. A method according to claim 7 wherein said permissive temperature is about 20° C. to about 25° C. and said restrictive temperature is about 35° C. to about 37° C.

9. A method according to claim 7 wherein the preincubation period of time is two hours.

10. A method according to claim 7 further comprising adding to a culture of said strain a known spindle pole body inhibitor as a control thereby providing a second control culture, preincubating the second control culture for the preincubation period of time at the permissive temperature, incubating the second control culture at the restrictive temperature, and comparing spindle body formation inhibition in the second control culture to inhibition in the presence of the sample agent.

11. A method according to claim 10 wherein said sample culture, said corresponding first control culture containing no sample agent, and said second control culture containing the known spindle pole body inhibitor comprise different portions of a single solidified culture in a dish or plate, and growth is observed visually by inspection of the dish or plate.

12. A method according to claim 1 wherein said sample culture and said corresponding first control culture containing no sample agent comprise different portions of a single solidified culture in a dish or plate, and growth is observed visually by inspection of the dish or plate.

13. A method for screening for the presence or absence of spindle pole body inhibition by a chemical or biochemical test sample which comprises:
    (a) adding a chemical or biochemical test sample to an area on a solidified culture of *Saccharomyces cerevisiae* containing a conditional mutant strain of *S. cerevisiae* which produces excess numbers of spindle pole bodies;
    (b) preincubating said culture for a period of time under permissive conditions sufficient to observe yeast cell growth by the conditional mutant strain;
    (c) incubating said culture for a period of time under restrictive conditions sufficient to inhibit yeast cell growth by the conditional mutant strain;
    (d) comparing the extent of growth in the culture in the vicinity of test sample with the extent of growth in the rest of the culture; and
    (e) determining the presence of said spindle pole body inhibition by observation of whether growth in the vicinity of test sample exceeds growth in the rest of the culture.

14. A method according to claim 13 wherein said *S. cerevisiae* strain is an esp1 mutant.

15. A method according to claim 14 wherein said *S. cerevisiae* strain is a cdc-esp1 double mutant.

16. A method according to claim 14 wherein said strain is a temperature-sensitive diploid *S. cerevisiae* strain homozygous for the esp1-1 mutation.

17. A method according to claim 16 wherein said permissive conditions comprise a temperature of about 20° C. to about 25° C. and said restrictive conditions comprise a temperature of about 35° C. to about 37° C.

18. A method according to claim 16 wherein said strain is SN127d.

19. A method according to claim 13 further providing a positive control by adding, to another area of the culture, a known spindle pole body inhibitor.

20. A method for assaying for fungicidal activity by a chemical or biochemical test sample by screening for the presence or absence of spindle pole body inhibition by the test sample comprising:
   (a) preparing, in a dish or plate, a solidified culture of a *Saccharomyces cerevisiae* strain containing a conditional lethal temperature-dependent esp1-1 mutation which produces excess numbers of spindle pole bodies;
   (b) adding to said culture, on a disk or in a well, a chemical or biochemical test sample;
   (c) preincubating said culture for a period of time under a permissive temperature and conditions sufficient to observe yeast cell growth by the *S. cerevisiae* strain;
   (d) shifting the culture to a restrictive temperature and incubating for a period of time under conditions sufficient to observe continued yeast cell growth and a diminution or cessation of growth in the absence of the test sample:
   (e) comparing the extent of growth in the culture in the vicinity of the test sample with the extent of growth in the rest of the culture; and
   (f) determining the presence of said spindle pole body inhibition by observation of whether growth in the vicinity of the test sample exceeds growth in the rest of the culture.

21. A method according to claim 20 wherein said strain is a diploid *S. cerevisiae* strain homozygous for the esp1-1 mutation.

22. A method according to claim 21 wherein said permissive temperature is about 20° C. to about 25° C. and said restrictive temperature is about 35° C. to about 37° C.

23. A method according to claim 21 wherein said strain is SN127d.

* * * * *